United States Patent [19]

DiGiacomo et al.

[11] 4,436,899
[45] * Mar. 13, 1984

[54] LAYERED ORGANOPHOSPHORUS INORGANIC POLYMERS

[75] Inventors: Peter M. DiGiacomo, Mission Viejo; Martin B. Dines, Santa Ana, both of Calif.

[73] Assignee: Occidental Research Corporation, Irvine, Calif.

[*] Notice: The portion of the term of this patent subsequent to Mar. 17, 1998 has been disclaimed.

[21] Appl. No.: 60,076

[22] Filed: Jul. 24, 1979

Related U.S. Application Data

[63] Continuation-in-part of Ser. No. 945,971, Sep. 26, 1978, Pat. No. 4,232,146.

[51] Int. Cl.$^3$ .................. C08G 79/04; C08G 79/14
[52] U.S. Cl. .................. 528/395; 260/429.1; 260/429.2; 260/429.3; 260/429.5; 260/429 R; 260/435 R; 528/398
[58] Field of Search ............... 260/429.1, 429.2, 429.3, 260/429.5, 429 R, 435 R; 528/395, 398

[56] References Cited

U.S. PATENT DOCUMENTS

| | | | |
|---|---|---|---|
| 4,232,146 | 11/1980 | DiGiacomo et al. | 528/395 |
| 4,235,990 | 11/1980 | DiGiacomo et al. | 528/287 |
| 4,235,991 | 11/1980 | DiGiacomo et al. | 528/391 |
| 4,256,872 | 3/1981 | DiGiacomo et al. | 528/395 |
| 4,267,308 | 5/1981 | Parziale et al. | 528/395 |
| 4,276,409 | 6/1981 | DiGiacomo et al. | 528/362 |
| 4,276,410 | 6/1981 | DiGiacomo et al. | 528/373 |
| 4,276,411 | 6/1981 | DiGiacomo et al. | 260/429.5 |
| 4,298,723 | 11/1981 | DiGiacomo et al. | 528/271 |

*Primary Examiner*—Helen M. S. Sneed
*Attorney, Agent, or Firm*—Christie, Parker & Hale

[57] ABSTRACT

A process for the production of phosphorus-containing organo substituted inorganic polymers comprises reacting at least one organophosphorous or organophosphoric acid compound of the formula $$[(HO)_2OP]_nR \text{ or } [(HO)_2OPO]_nR$$

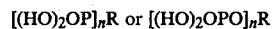

wherein n is 1 or 2 and R is an organo group covalently coupled to phosphorus with at least one tetravalent metal ion to precipitate a solid inorganic polymer in which the molar ratio of phosphorus to tetravalent metal is about 2 to 1 and in which the organo group is covalently bonded to phosphorus and phosphorus is linked to the tetravalent metal through oxygen.

4 Claims, 15 Drawing Figures

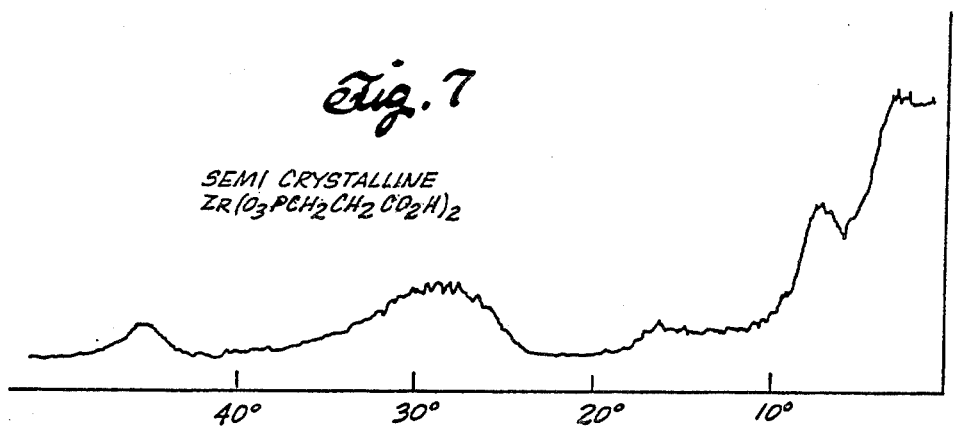
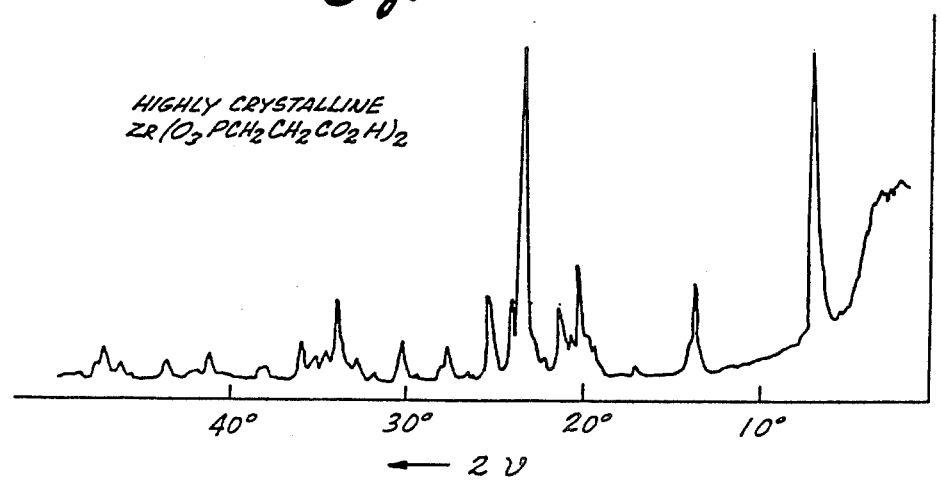

LAYERED ORGANOPHOSPHORUS INORGANIC POLYMERS

CROSS-REFERENCE TO RELATED APPLICATIONS

This application is a continuation-in-part of application Ser. No. 945,971, filed Sept. 26, 1978, now U.S. Pat. No. 4,232,146.

This application is related to the following copending U.S. applications:

| Filing Date | Serial Number or Title |
| --- | --- |
| October 17, 1978 | 952,228 |
| December 4, 1978 | 966,197 |
| January 29, 1979 | 7,275 |
| May 30, 1979 | Process for Preparing Layered Organophosphorous Inorganic Polymers |
| July 2, 1979 | Layered Organophosphorus Inorganic Polymers Containing Mercapto or Thio Groups |
| July 2, 1979 | Layered Cyano End Terminated Organophosphorus Inorganic Polymers | and to five applications filed concurrently herewith and titled: Layered Organoarsenous Inorganic U.S. Ser. No. 60,078 Polymers, Layered Organophorphorus Inorganic Polymers Containing Acyclic Groups, U.S. Ser. No. 60,079 Layered Organophosphorus Inorganic Polymers Containing Cyclic Groups, U.S. Ser. No. 60,077 Layered Organophosphorus Inorganic Polymers Containing Oxygen Bonded to Carbon, U.S. Ser. No. 60,249 and Layered Organophosphorus Inorganic Polymers Containing Mixed Functional Groups, U.S. Ser. No. 60,250 the entire disclosure of each application being incorporated herein by this reference.

BACKGROUND OF THE INVENTION

The present invention is directed to the preparation of solid inorganic polymers having organo groups anchored to the surfaces of the polymers. The majority of the polymers formed are layered crystals which display intercalation activity.

The interface surfaces of solids are responsive regions of chemical and physical action. In many practical chemical and physical phenomena such as absorption, corrosion inhibition, heterogeneous catalysis, lubrication, ion exchange activity, adhesion and wetting, and electrochemistry, activity occurs as a consequence of the presence of a definable solid surface. Solids agents are preferred in most processes over solution or homogeneously dispersed reactive alternatives primarily because they greatly simplify efficient separation of products from reactants. However, solids invariably suffer from deficiencies in activity and selectivity in the conversions they effect, due to inherent heterogeneity in their active sites which arises from the nature of their surface structure. Furthermore, much of the active sites are usually buried within the surface, and as a result of these two factors, elevated temperature and low conversions are typically encountered. Exceptions in which homogeneous catalysts are employed have been the Monsanto process for the production of acetic acid from methanol and carbon monoxide employing rhodium, the production of linear alcohols from olefins and syngas, ethylene oxidation by the Wacker process, catalysis of olefins to form polymers, and other polymerization systems.

In an effort to achieve the best features of both homogeneous and heterogeneous processes, efforts have been made to chemically "anchor" known effective solution agents such as phosphines, nitriles, cyclopentadiene and the like, onto certain solids. Porous inorganic surfaces and insoluble organic polymers have been employed. Silica has been the inorganic of choice, the bonded ligand being attached by reaction with the —OH groups projecting from the surface. The organic polymer most used has been polystyrene, with an appropriate metal-coordinating function bonded via the phenyl rings. Results have been generally encouraging. However, there have been pervasive problems deriving from the non-uniform situation of sites which has manifested itself in loss of expected selectivity, activity and even in attrition.

Many inorganic solids crystallize with a layered structure and some could present sites for anchoring active groups. In this form, sheets or slabs with a thickness of from one to more than seven atomic diameters lie upon one another. With reference to FIG. 1, strong ionic or covalent bonds characterize the intrasheet structure, while relatively weak van der Waals or hydrogen bonding occurs between the interlamellar basal surfaces, in the direction perpendicular to their planes. Some of the better known examples are prototypal graphite, most clay minerals, and many metal halides and sulfides. A useful characteristic of such materials is the tendency to incorporate "guest" species in between the lamella.

In this process, designated "intercalation", the incoming guest molecules, as illustrated in FIG. 2, cleave the layers apart and occupy the region between them. The layers are left virtually intact, since the crystals simply swell in one dimension, i.e., perpendicular to the layers. If the tendency to intercalate is great, then the host layered crystal can be thought of as possessing an internal "super surface" in addition to its apparent surface. In fact, this potential surface will be greater than the actual surface by a factor of the number of lamella composing the crystal. This value is typically on the order of $10^2$-$10^4$. Although edge surface is practically insignificant compared to basal surface, it is critical in the rate of intercalation, since the inclusion process always occurs via the edges. This is because bonding within the sheets is strong, and therefore, basal penetration of the sheets is an unlikely route into the crystal.

Previous studies of the intercalative behavior of layered compounds have mainly been conducted by solid-state chemists interested in the bulk effects on the layered host materials. Graphite has, for example, been extensively studied from an electronic point of view. In general, the function of the host is essentially passive. That is, on intercalation the host serves as the matrix or surface with which the incoming guest molecules interact, but throughout the process and on deintercalation the guests undergo only minor perturbation.

In order for a more active process to occur during intercalation, such as selective complexation or catalytic conversion, specific groups must be present which effect such activity. There might also be some preferable geometric environment about each site, as well as some optimal site-site spacing. These considerations have not been extensively applied to intercalation chemistry simply because such kinds of active groups required are not found on layered surfaces.

An approach in which catalytically active agents have been intercalated into graphite or clays for subsequent conversions has been described in "Advanced Materials in Catalysis", Boersma, Academic Press, N.Y. (1977), Burton et al, editors, and "Catalysis in Organic Chemistry", Pinnavia, Academic Press, N.Y. (1977), G. V. Smith, editor, each incorporated herein by reference. In neither case could it be shown that any activity was occurring within the bulk of the solid. Rather, it is believed that edge sites are responsible for the reactivity observed. In none of the cases was the active site covalently anchored, or fixed upon the lamella of the host. Instead, the normal ionic or van der Waals forces of intercalated guests were operating.

One of the few layered compounds which have potential available sites is zirconium phosphate $Zr(O_3POH)_2$. It exists in both amorphous and crystalline forms which are known to be layered. In the layered structure, the site-site placement on the internal surfaces is about 5.3 Å, which leads to an estimated 25 Å$^2$ area per site. This area can accomodate most of the functional groups desired to be attached to each site. The accepted structure, symbolized projection of a portion of a layer of this inorganic polymer and a representation of an edge view of two layers, are shown respectively in FIGS. 3, 4 and 5.

Besides the advantageous structural features of zirconium phosphate, the material is chemically and thermally stable, and non-toxic.

Quite a bit of work has been conducted on the zirconium phosphate, mainly because it has been found to be a promising inorganic cation exchanger for alkali, ammonium and actinide ions, Alberti, "Accounts of Chemistry Res."11, 163, 1978, incorporated herein by reference. In addition, some limited work has been described on the reversible intercalation behavior of layered zirconium phosphate toward alcohols, acetone, dimethylformamide and amines, Yamaka and Koizuma, "Clay and Clay Minerals" 23, 477 (1975) and Michel and Weiss, "Z. Natur," 20, 1307 (1965) both incorporated herein by reference. S. Yamaka described the reaction of this solid with ethylene oxide, which does not simply incorporate between the layers as do the other organics, but rather was found to irreversibly react with the acidic hydroxyls to form a covalant bonded product, Yamaka, "Inorg. Chem" 15, 2811, (1976). This product is composed of a bilayer of anchored ethanolic groups aimed into interlayers. The initial layer-layer repeat distance is expanded from about 7.5 Å to 15 Å, consistent with the double layer of organics present. The overall consequence of this reaction is to convert inorganic acid hydroxyls to bound organic alkanol groups. This conversion, while of interest, has limited if any improvement over the hydroxyls already available on zirconium phosphate.

Recent reports by Alberti et al, J. Inorg. Nucl. Chem. 40, 1113 (1978) and Maya, Inorg. Nucl. Chem. Letters, 15, 207 (1979) have described a method similar to that described herein for the preparation of similar layered compounds, and Maya has demonstrated usefulness as stationary phases or supports in chromatography.

SUMMARY OF THE INVENTION

According to the present invention there is provided a process for the production of inorganic polymers having organo groups covalently bonded to phosphorus atoms and in which the phosphorus atoms are, in turn, covalently bonded by an oxygen linkage to tetravalent metal atoms and when formed in a layered crystalline state provided the organo groups on all of the apparent and interlamellar surfaces.

The process of the invention comprises a liquid media reaction in which at least one organophosphorus acid compound of the formula:

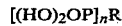
$[(HO)_2OP]_nR$ wherein n is 1 or 2 and R is an organo group covalently coupled to the phosphorus atom, and wherein when n is 2, R contains at least two carbon atoms and is directly or indirectly coupled to phosphorus atoms through different carbon atoms whereby the two phosphorus atoms are separated by at least two carbon atoms, is reacted with at least one tetravalent metal ion selected from the group consisting of zirconium, cerium, thorium, uranium, lead and titanium, the molar ratio of phosphorus to the tetravalent metal is 2 to 1. Reaction preferably occurs in the presence of an excess of the organophosphorus acid compound and the metal ion is provided as a compound soluble in the liquid media.

Where only one specie of an organophosphorus acid compound is provided as the reactant with the tetravalent metal compound, the end product will have the empirical formula $M(O_3PR)_2$. Phosphoric and/or phosphorous acid can also be present as reactive diluents to form part of the solid inorganic polymeric structure which is the product of the reaction.

The products formed are layered crystalline to amorphous in nature. For all products, the R groups may be directly useful or serve as intermediates for the addition of substitution of other functional groups. When the product is crystalline and n is 2, cross-linking between the interlamellar layers occurs.

The normal liquid media is water. However, organic solvents, particularly ethanol, may be employed where water will interfere with the desired reaction. Preferably, the solvent is the solvent in which the organophosphorus acid compound is prepared. Where the organophosphorus acid compound has a sufficiently low melting point, it can serve as the liquid media.

The metathesis reaction occurs at temperatures up to the boiling point of the liquid media at the pressures involved, typically from ambient to about 150° C. and more preferably from ambient to about 100° C. While formation of the solid inorganic polymer is almost instantaneous, the degree of crystallinity of the product can be increased by refluxing the reaction products for times from about 5 to 15 hours. Crystallinity is also improved by employing a sequestering agent for the tetravalent metal ion.

THE DRAWINGS

Figure 1:
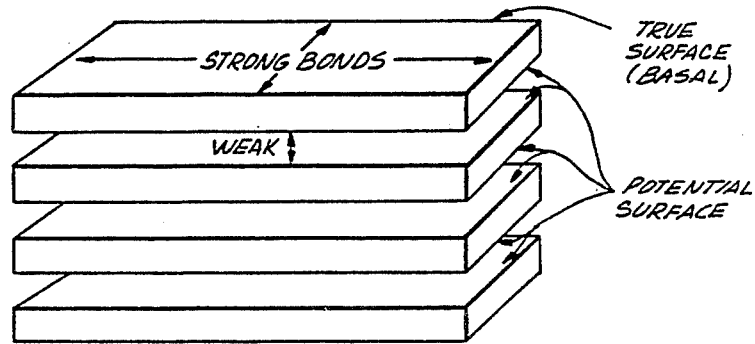
FIG. 1 illustrates a layered microcrystal. Each lamellar slab is formed of strong covalent bonds and has a thickness of about 10 atoms.
Figure 2:
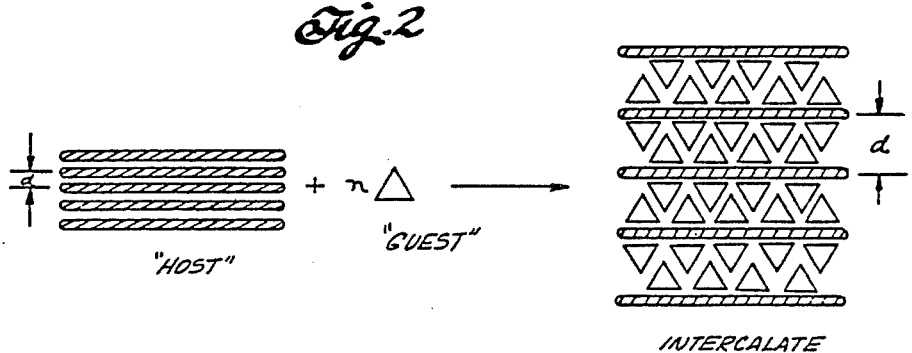
FIG. 2 illustrates intercalation where the interlayer distance is shown as "d."
Figure 3:
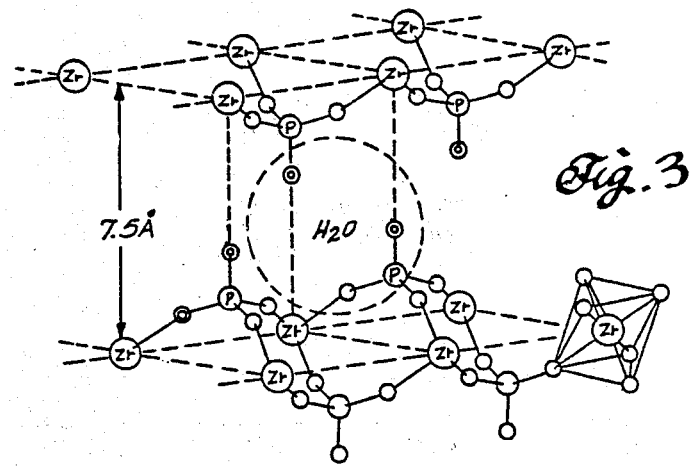

FIG. 3 illustrates the accepted structure for zirconium phosphate and spacing between layers. The dashed lines between zirconium (Zr) atoms is to establish the plane between them. In the drawing P=Phosphorus, O=Oxygen and water is hydration is shown.

Figure 4:
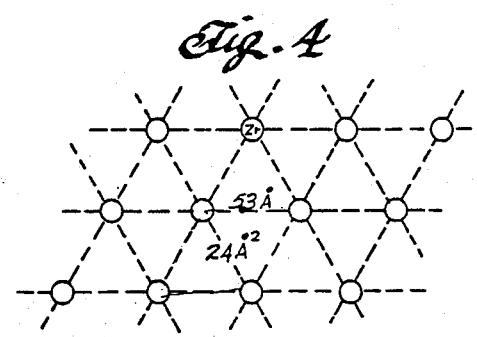

FIG. 4 illustrates a projection of zirconium plane showing accepted spacing between Zr atoms and the available linkage area.

Figure 5:
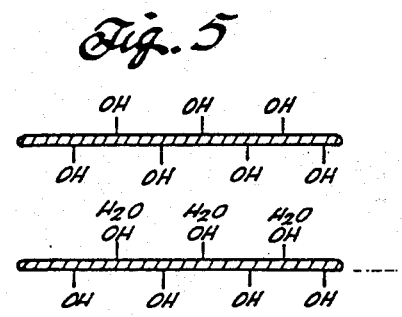

FIG. 5 is a symbolized depiction of spaced zirconium phosphate layers showing covalently bonded hydroxyl groups and water of hydration.

Figure 6:
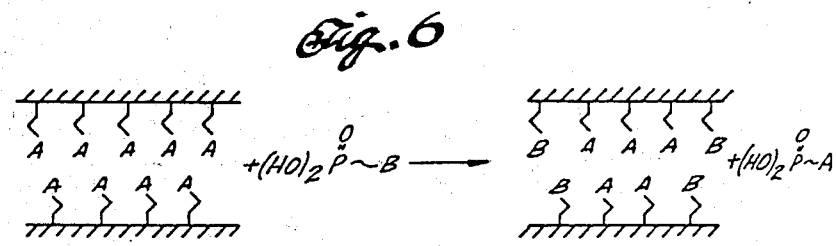

FIG. 6 illustrates an exchange reaction between anchored groups "A" and groups to be substituted for "B", and ⌒ represents the portion of the organo group linking the terminal group "A" or "B" to the crystals or the organophosphorus acid compound reactant.

FIG. 7 is an x-ray powder diffraction pattern for semi-crystalline zirconium 2-carboxyethyl phosphonate as prepared in Example 1.

FIG. 8 is an x-ray powder diffraction pattern for highly crystalline zirconium 2-carboxyethyl phosphonate as prepared in Example 2.

Figure 9:
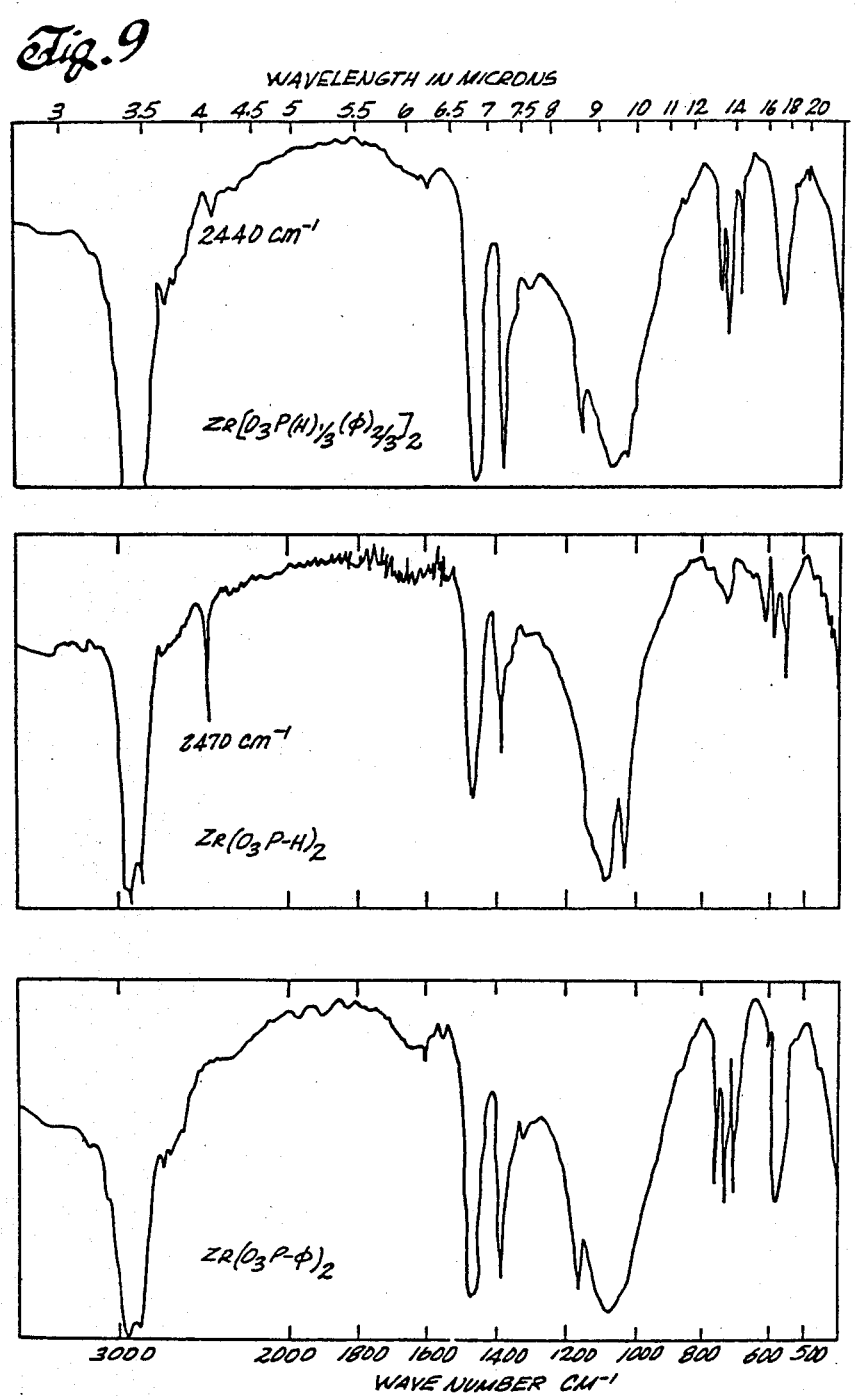

FIG. 9 is infrared spectra for a mixed component product $Zr(O_3P(H)_{1/3}, \phi_{2/3})_2$ as compared to the pure phases $Zr(O_3P\phi)_2$ and $Zr(O_3PH)_2$ where $\phi$ is the radical $—C_6H_5$.

Figure 10:
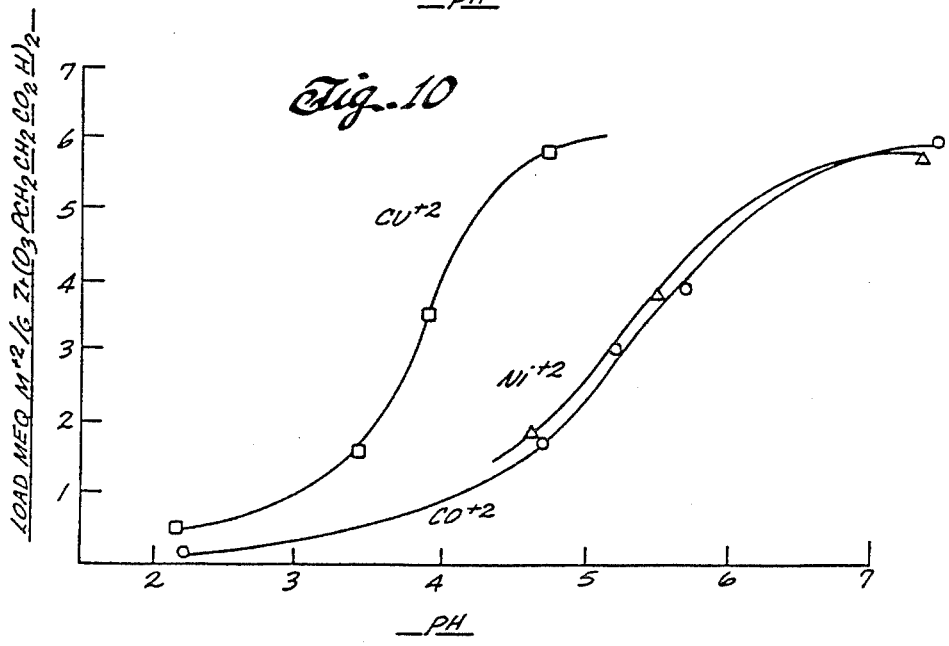

FIG. 10 compares the loading of divalent metals on zirconium 2-carboxyethyl phosphonate as a function of pH.

Figure 11:
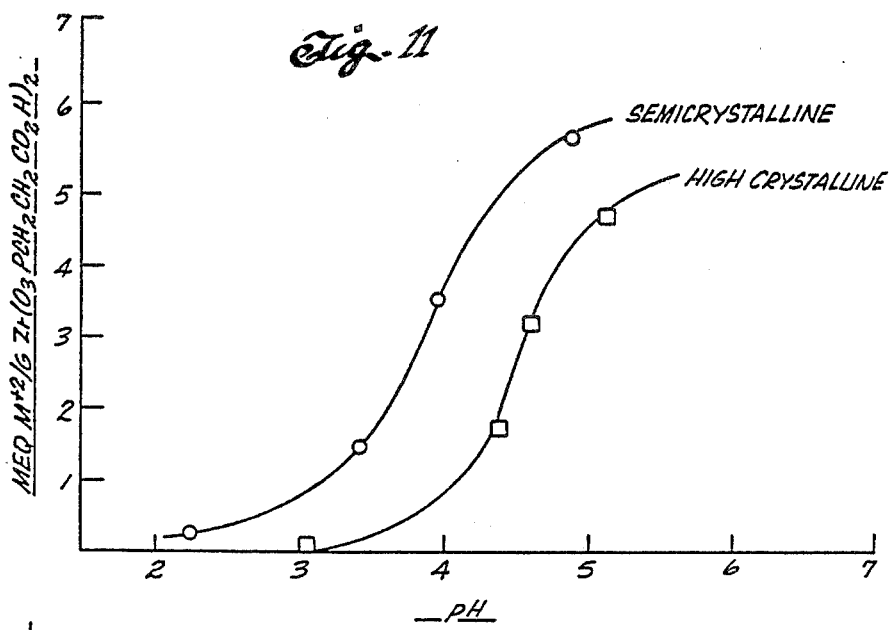

FIG. 11 compares the loading of $Cu^{+2}$ in the semi-crystalline reaction product of Example 1 to the highly crystalline product of Example 2.

Figure 12:
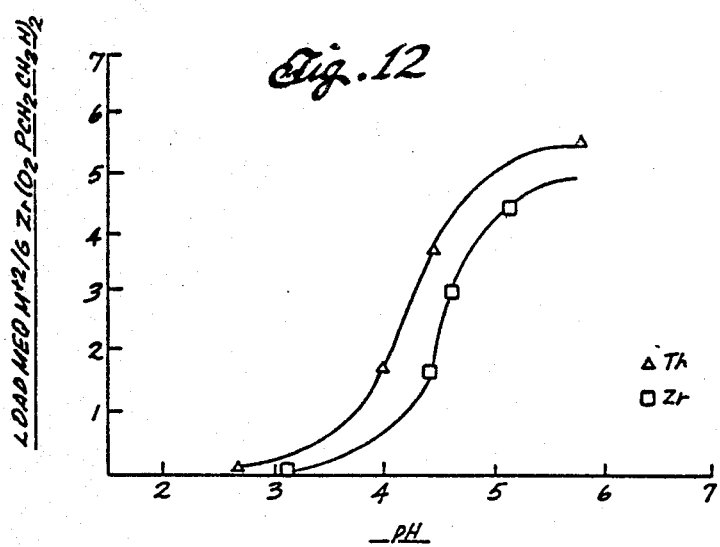

FIG. 12 compares the loading of $Cu^{+2}$ on the reaction product of Example 2 to thorium 2-carboxyethyl phosphonate.

Figure 13:
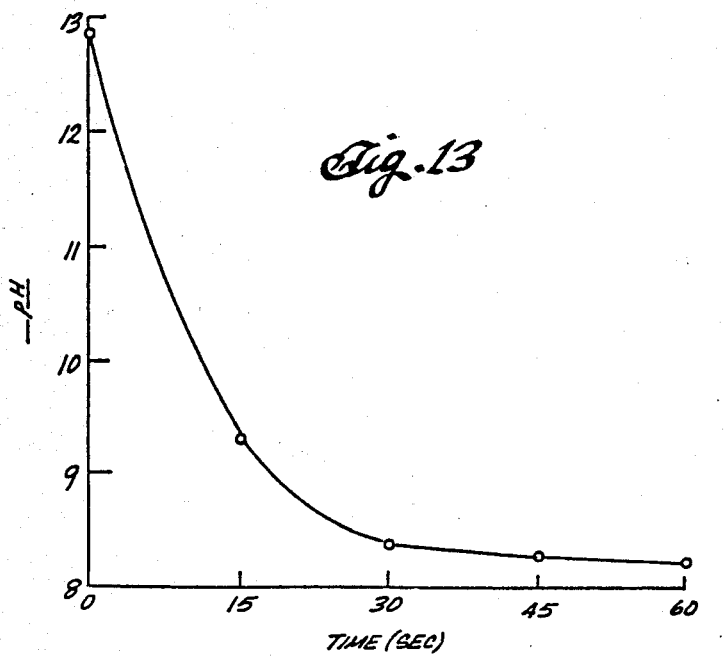

FIG. 13 shows the rate of neutralization of zirconium 2-carboxyethyl phosphonate by sodium hydroxide.

Figure 14:
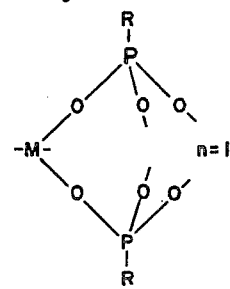

FIG. 14 shows the basic structural unit of the inorganic polymer formed by the process of the invention where n is 1 and where P=phosphorus atom, O=oxygen atom, M=tetravalent metal atom and R is the organo group.

Figure 15:
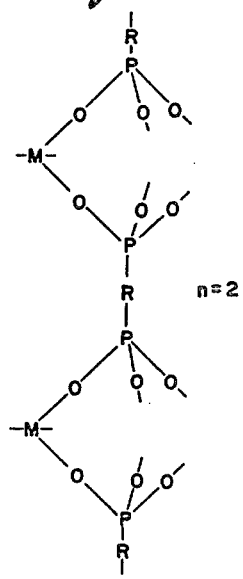

FIG. 15 shows the basic structural unit of the inorganic polymer formed by the process of the invention where n is 2 and where P=phosphorus atom, O=oxygen atom, M=tetravalent metal atom and R is the organo group.

DETAILED DESCRIPTION

According to the present invention there is provided a process for the production of inorganic polymers in layered crystalline to amorphous state by the liquid phase metathesis reaction of at least one organophosphorus acid compound having the formula:

$$[(HO)_2OP]_nR$$

wherein n is 1 or 2 and R is an organo group covalently coupled to the phosphorus atom with at least one tetravalent metal ion selected from the group consisting of zirconium, thorium, cerium, uranium, lead and titanium to form a solid inorganic polymer precipitate in which phosphorus is linked to the metal by oxygen and the organo group is covalently bonded to the phosphorus atom. Where, in the organophosphorus compound, n is 2, the end product occurs in the bis configuration. In this configuration, R must contain two or more carbon atoms, preferably from two to about twenty carbon atoms, such that at least two carbon atoms separate the phosphorus atoms. In this bis configuration no single carbon atom is bound directly or indirectly to more than one [PO(OH)$_2$] group. When n is 1, and as depicted in FIG. 14, the organo groups will be pendant from phosphorus atoms. When n is 2, and as depicted in FIG. 15, cross-linking will occur between interlamellar surfaces of the crystalline end product. Typically, the tetravalent metal ion is provided as a soluble salt MX$_4$ wherein M is as defined above and X is the anion(s) of the salt. Typical anions include halides, $HSO_4^{-1}$, $SO_4^{-2}$, $O_2C—CH_3^{-1}$, $NO_3^{-1}$, $O^{-2}$ and the like.

The majority of the polymeric reaction products formed are found to be layered crystalline or semi-crystalline in nature and, as such, provide layered structures similar to zirconium phosphates. The remainder are amorphous polymers possessing a large quantity of available pendant groups similar to silica gel.

By the term "organophosphorus acid compound", as used herein, there is meant a compound of the formula:

$$[(HO)_2OP]_nR$$

wherein n is 1 or 2, R is any group which will replace a hydroxyl of phosphoric acid and/or the hydrogen of phosphorus acid and couple to the acid by a covalent bond. Coupling to the acid may be through carbon, oxygen, silicon, sulfur, nitrogen and the like. Coupling through carbon or an oxygen-carbon group is presently preferred.

When, in the organophosphorus compound, n is 2, the end product occurs in the bis configuration. In this configuration, R must contain two or more carbon atoms, preferably from two to about twenty carbon atoms, such that at least two carbon atoms separate the phosphorus atoms. In this bis configuration, no single carbon atom is bound directly or indirectly to more than one [PO(OH)$_2$] group. Thus the groups which link to the metal have the basic structural formula:

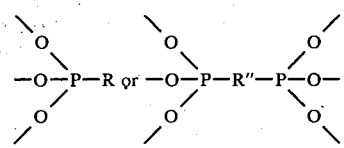

wherein R" is a bis group containing at least two carbon atoms bonded directly or indirectly to phosphorus and such that no phosphorus atoms are bonded directly or indirectly to the same carbon atom. The basic structures of the inorganic polymer forms are shown in FIGS. 14 and 15.

When coupling is through carbon, the organo phosphorus acid compound is an organo phosphonic acid and the product a phosphonate. When coupling is through oxygen-carbon, the organophosphorus acid compound is an organo-phosphoric monoester acid and the product a phosphate.

The general reaction for phosphonic acids alone is shown in equation (1) below and for monoesters of phosphoric acid alone by equation (2).

$$M^{+4}+2(HO)_2OPR \rightarrow M(O_3P—R)_2 +4H^+ \tag{1}$$

$$M^{+4}+2(HO)_2OP—OR' \rightarrow M(O_3P—OR')_2 +4H^+ \tag{2}$$

wherein R' is the remainder of the organo group.

The product contains phosphorus to metal in a molar ratio of about 2 to 1, and the empirical formula for the product would show all groups bound to phosphorus.

While nowise limiting, the R groups attachable to phosphorus may be saturated and unsaturated, substituted and unsubstituted and include, among others, alkylene, alkyloxy, alkyne, aryl, haloalkyl, alkylaryl, aryloxy, mercaptoalkyl, aminoalkyl, carboxyalkyl, morpholinoalkyl, sulfoalkyl, phenoxyalkyl, beta-diketo alkyl, cyanoalkyl, cyanoalkoxy, and the like. In general, the organo group should occupy an area of no more than about 25 Å square for proper spacing. Larger groups may be employed when mixed reagents are used.

The process for the formation of the novel inorganic polymers is a metathesis reaction conducted in the presence of a liquid medium receptive to the tetravalent metal ion at a temperature up to the boiling point of the liquid medium, preferably from ambient to about 150° C. and, more preferably, to about 100° C. at the pressure employed.

While water is the preferred liquid medium, as most of the organophosphorus acid compounds are hydroscopic, an organic solvent such as ethanol may be employed, where water interferes with the reaction. There need only to be provided a solvent for the organophosphorus acid compound since the tetravalent ion can be dispersed as a solid in the solvent for slow release of the metal ion for reaction with the organophosphorus acid compound. If it has a sufficiently low melting point, the organophosphorus acid compound may serve as a solvent. Typically, the liquid medium is the liquid medium in which the organophosphorus acid is formed.

For complete consumption of the tetravalent compound, the amount of acid employed should be sufficient to provide two moles of phosphorus per mole of tetravalent metal. An excess is preferred. Phosphorous acid and/or phosphoric acid, if present, will enter into the reaction and provide an inorganic polymer diluted in respect of the organo group in proportion to the amount of phosphorus or phosphoric acid employed.

Reaction is virtually instantaneous at all temperatures leading to precipitation of layered crystalline, semi-crystalline or amorphous inorganic polymer solid.

The amorphous phase appears as a gel similar to silica gel. The gel can be crystallized by extended reflux in the reaction medium, usually from about 5 to about 15 hours. The semi-crystalline product is characterized by a rather broad x-ray powder pattern. (See FIGS. 7 and 8.)

The presence of sequestering agents for the metal ion slows down the reaction and also leads to more highly crystalline products. For instance, a semi-crystalline solid was prepared by the aqueous phase reaction of zirconium chloride and excess 2-carboxyethyl phosphonic acid, followed by 15 hours of reflux. A highly crystalline modification was prepared under identical conditions except that hydrogen fluoride was added to the reaction mixture. A slow purge of $N_2$ over the surface of the reaction solution slowly removed the fluoride from the system. Fluoride is a very strong complexing agent for zirconium ions. The slow removal of fluoride results in slow release of the metal ion for reaction with the phosphonic acid, resulting in an increase in crystallinity.

A similar enhancement of crystallinity was obtained in the reaction of thorium nitrate with 2-carboxyethyl phosphonic acid. Nitrate ion is a sequestering agent for thorium and the rate of formation of this product is slow and the product polymer quite crystalline.

As compared to zirconium phosphate forming crystals of 1–5 microns, the crystals of 100 to greater than 1000 micron in size have been prepared in accordance with the invention.

A property critical for many of the likely uses of the products is their thermal stability. This is because deficiencies in activity can be compensated for by reasonable increases in operating temperature. A standard method for thermal characterization is thermal gravimetric/differential thermal analysis (TGA/DTA). These techniques indicate changes in weight and heat flow of substances as a function of temperature. Thus, decomposition and phase changes can be monitored as temperature increases.

Zirconium phosphate itself is quite a stable material. Interlayer water is lost at about 100° C., and a second dehydration involving the phosphates occurs above 400° C. The practical ion-exchanging abilities are lost in this step.

The inorganic polymers of this invention are also stabilized toward thermal decomposition as compared to pure organic analogs as a result of the fixation and separating effect of the inorganic support.

For zirconium chloromethyl phosphonate, for instance, weight loss did not commence until well above 400° C. The organic fragment was half lost at about 525° C., indicating remarkable stability. Decomposition of zirconium 2-carboxyethylphosphonate begins between 300° and 400° C. The decomposition process inflection point, approximate midpoint, falls at about 400° C.

While not bound by theory, phosphates probably decompose like carboxylic esters to yield acid and unsaturates, whereas phosphonates likely form radicals by homolytic cleavage. Both nitrophenyl and cyanoethyl phosphates of zirconium decompose at about 300 ° C. The phenylphosphonate decomposes at about 425° C.

Besides proving the suitability of such compounds in elevated temperature applications, the TGA analysis affirmed covalent bonding to phosphorus. This is because normal intercalative interactions are reversed within 10°–100° C. above the boiling point of the guest.

The process of this invention permits a wide variety of inorganic polymers to be formed having the characteristic of the organo group protected by the inorganic polymer structure and with subsequent exchange or substitution reactions, the formation of other inorganic polymers. Polymers formed may be block, random and the like.

For instance, a mixture of phenyl phosphonic acid and phosphorous acid was simultaneously reacted with zirconium ion to yield a single solid phase. The interlamellar distance was the same as zirconium phenyl phosphonate, or about 15.7 Å. There was no reflection at 5.6 Å, the normal spacing for zirconium phosphite. This established that the largest group should determine interlamellar distance and indicated that a discreet zirconium phosphate phase was not present. Evidence of a change in chemical environment of P-H band was established by infrared analysis. In infrared analysis of zirconium phosphite, P-H stretching is observed as a sharp band at 2470 cm$^{-1}$ (moderate intensity). In the mixed compound solid, this band was shifted to 2440 cm$^{-1}$ and broadened.

Another route is to exchange one pendant group for another. The exchange reaction is descibed in Example 31. While not bound by theory, the present expected points of exchange are at the periphery of the crystal and are schematically illustrated in FIG. 6. Such bifunctional materials exhibit the quality of providing terminal groups for attracting species for intercalation and then interaction with the internal groups.

The reaction of bis acids with tetravalent metal ions permits interlamellar cross-linking by a reaction such as $(HO)_2OPCH_2CH_2OP(OH)_2 + M^{+4} \rightarrow ]-CH_2CH_2-[$ where as in FIG. 6, ⟆⟆⟆⟆⟆⟆ represents the interlamallar layers to which the alkyl group is anchored. As with all organo groups, for the bis configuration at least two carbon atoms are present, preferably from two to twenty atoms, and the phosphorus atoms are linked directly or indirectly to different carbon atoms. Since size of the linking group will control and fix interlamellar spacing, there is provided effective laminar sieves of fixed spacing for application analogous to that of molecular sieves.

Ion exchange activity was established with pendant carboxylic acid groups. Prepared zirconium 2-carboxyethyl phosphonate was established to have an interlayer distance of 12.8 Å. When intercalated to form its n-hexylammonium salt interlayer distance increased to 27.2 Å. When sodium was taken up, layer spacing increased to 14.2 Å. X-ray and infrared data indicated the highly crystalline inorganic polymer to behave as expected for carboxylic acid with behavior analogous to ion exchange resins except that both external and internal surfaces were functional establishing them as super surface ion exchange resins. Moreover, since the inorganic polymers can be prepared as microcrystalline powders, diffusion distances are short.

As summarized in Table 1, nitrile and mercapto anchored groups show the ability to take up silver and copper ions at room temperature for catalytic activity.

TABLE 1

| Anchored Group | Metal Ion | Loading MMole Metal MMole Zr |
|---|---|---|
| —O~CN | 0.1 M Ag+ | 0.20 |
| ~SH | 0.1 M Ag+ | 1.0 |
| —O~CN | 0.1 M Cu++ | 0.10 |
| —O~CN | 0.1 M Cu++ 0.5 M HOAc 0.5 M NaAc | 0.10 |

~ = groups formed of carbon and hydrogen.
Ac = acetate radical

The alternate to catalytic utility is to attach the metals to the organophosphorus acid prior to reaction with the soluble tetravalent metal compound, The high surface area of the crystalline products also make them utile for sorption of impurities from aqueous and non-aqueous media.

Another utility is as an additive to polymeric compositions. Similar to the high aspect ratio provided by solids such as mica which improve the stress strain properties of the polymers, the powdered inorganic polymer products of the invention can serve the same function and add features. By the presence of reactive end groups on the bonded organo groups, chemical grafting to the polymer network can be achieved to increase composite crystallinity and elevate heat distortion temperature. In addition, the presence of phosphorus induces flame retardant properties, as would bound halogen.

Still other utilities include solid lubricants which behave like mica, graphite and molybdenum disulfide; solid slow release agents where intercalated materials can be slowly leached or released from the internal layers of the crystals; substance displaying, electrical, optical phase or field changes with or without doping and the like.

While nowise limiting, the following Examples are illustrative of the preparation of solid inorganic polymers of this invention and some of their utilities.

In the Examples conducted in the atmosphere no extraordinary precautions were taken concerning oxygen or moisture. Reagents were usually used as received from suppliers. The products formed are insoluble in normal solvents and do not sublime. However, the combined weight of yield data, spectroscopy, elemental analyses, TGA and powder diffraction results confirm the compositions reported with good reliability.

X-ray powder patterns were run on a Phillips diffractometer using CuK radiation.

Thermal analyses were conducted on a Mettler instrument. Infrared spectra were obtained with a Beckmann Acculab spectrophotometer.

Surface area were determined using both a dynamic flow method, on a Quantasorb instrument, and also with a vacuum static system on a Micromeritic device. Both employ a standard BET interpretation of nitrogen coverage.

Titrations were carried out in aqueous or alcoholic medium. A standard combination electrode and an Orion Ionalyzer pH meter were used for pH determination. The titration of the solid interlamellar anchored materials is analogous to the titration of an ion exchange resin.

EXAMPLE 1

To a 250 ml 3-necked flash fitted with a reflux condenser, stirrer, thermometer and heating mantle, there was charged 21.8 ml of a 38% aqueous solution providing 11.1 g of 2-carboxyethylphosphonic acid in 25 ml of water. Stirring was commenced at room temperature and 9.2 grams of $ZrOCl_2$ in 10 ml of water was added. A white precipitate was immediately formed. Water (17 ml) was added to fluidize the solids and the temperature was raised to about 90° to about 100° C. to a gentle reflux which was continued for 15 hours. The slurry was cooled to room temperature and the white solid isolated by filtration. The solid was washed on the filter with water, acetone, then ether. The solid product was dried to a constant weight of 12.1 grams determined to be semi-crystalline and to have the empirical formula $Zr(O_3PCH_2CH_2COOH)_2$. The x-ray powder diffraction pattern is shown in FIG. 7.

EXAMPLE 2

The procedure of Example 1 repeated except that 4 ml of a 48% aqueous solution of hydrogen fluoride was added to the initial mixture and slowly removed by a slow purge of nitrogen maintained during reflux. The observed to calculated atomic composition was as follows:

| Atom | Observed | Calculated |
|---|---|---|
| C | 18.4% | 18.23% |
| H | 2.84% | 2.54% |
| P | 15.5% | 15.7% |

The x-ray diffraction pattern for the highly crystalline product is shown in FIG. 8. Interlayer spacing was determined to be 12.8 Å.

EXAMPLE 3

Using the procedure of Example 1, there was reacted 46 grams of chloromethylphosphonic acid and 5.5 grams of ZrOCl$_2$.8H$_2$O to yield 5.9 grams of a crystalline solid having the empirical formula Zr(O$_3$PCH$_2$Cl)$_2$ with an interlayer spacing of 10.5 Å.

EXAMPLE 4

Example 3 was repeated except that 10 grams of chloromethylphosphonic acid was reacted with 6.6 grams of Th(NO$_3$)$_4$.4H$_2$O to yield 6.0 grams of crystalline solid having the empirical formula Th(O$_3$PCH$_2$Cl)$_2$ with an interlayer spacing of 10.5 Å.

EXAMPLE 5

Example 4 was repeated except that 12.2 grams of chloromethylphosphonic acid was reacted with 3.9 grams of PbO$_2$ to yield 5.1 grams of a crystalline solid having the empirical formula Pb(O$_3$PCH$_2$Cl)$_2$ with an interlayer spacing of 9.83 Å.

EXAMPLE 6

Example 4 was repeated except that 0.55 gram of chloromethylphosphonic acid was reacted with 0.34 gram of UCl$_4$ to yield 0.4 gram of a crystalline solid having the empirical formula U(O$_3$PCH$_2$Cl)$_2$ with an interlayer spacing of 10.0 Å.

EXAMPLE 7

Example 4 was repeated except that 4.74 grams of chloromethylphosphonic acid was reacted with 4.4 grams of titanium tetrachloride to yield 5.9 grams of a crystalline solid having the empirical formula Ti(O$_3$PCH$_2$Cl)$_2$ with an interlayer spacing of 10.4 Å.

EXAMPLE 8

Using the procedure of Example 1, there was reacted 1.99 grams of phenylphosphonic acid with 1.96 grams of ZrOCl$_2$.8H$_2$O to yield 2.56 grams of a crystalline solid having the empirical formula Zr(O$_3$PC$_6$H$_5$)$_2$ with an interlayer spacing of 14.9 Å. Dynamic surface area was 186 m$^2$/g and static surface area was 220 m$^2$/g.

EXAMPLE 9

Example 8 was repeated except that 2.03 grams of phenylphosphonic acid was reacted with 3.48 grams of Th(NO$_3$)$_4$.4H$_2$O to yield 3.44 grams of a crystalline solid having the empirical formula Th(O$_3$PC$_6$H$_5$)$_2$ with an interlayer spacing of 14.7 Å. Dynamic and static surface areas were in each instance 67 m$^2$/g.

EXAMPLE 10

Example 8 was repeated except that 0.9 gram of phenylphosphonic acid was reacted with 0.7 gram of Ce(HSO$_4$) to yield 1.3 grams of a crystalline solid having the empirical formula Ce(O$_3$PC$_6$H$_5$)$_2$ with an interlayer spacing of 15.5 Å.

EXAMPLE 11

Example 8 was repeated except that 1.67 grams of phenylphosphonic acid was reacted with 1.0 grams of titanium tetrachloride. There was formed 1.94 grams of a crystalline solid of the empirical formula Ti(O$_3$PC$_6$H$_5$)$_2$ with an interlayeer spacing of 15.2 Å. Dynamic surface area was 151 m$^2$/g and static surface area was 167 m$^2$/g.

EXAMPLE 12

As in Example 1, there was reacted about 10 grams of mercaptomethylphosphonic acid with 6.3 grams of ZrOCl$_2$.8H$_2$O to yield 7.3 grams of an amorphous solid having the empirical formula Zr(O$_3$PCH$_2$SH)$_2$.

EXAMPLE 13

As in Example 1, there was reacted 2.0 grams of 2-mercaptoethylphosphonic acid with 1.0 gram of ZrOCl$_2$ to yield 1.72 grams of a crystalline solid having the empirical formula Zr(O$_3$PCH$_2$CH$_2$SH)$_2$ and with an interlayer spacing of 15.5 Å.

EXAMPLE 14

As in Example 1, there was reacted 0.50 gram of 2-aminoethylphosphonic acid with 0.64 grams of ZrOCl$_2$.8H$_2$O to yield 0.82 gram of a crystalline solid having the empirical formula Zr(O$_3$PCH$_2$CH$_2$NH$_2$)$_2$.

EXAMPLE 15

As in Example 1, there was reacted 1.9 grams of 2-carboxyethylphosphonic acid with 2.3 grams of Th(NO$_3$)$_4$.4H$_2$O to yield 1.97 grams of a crystalline solid having the empirical formula Th(O$_3$PCH$_2$CH$_2$COOH)$_2$ with an interlayer spacing of 14.2 Å.

EXAMPLE 16

As in Example 1, there was reacted 16.1 grams for 2-carboxymethylphosphonic acid with 13.5 grams of ZrOCl$_2$.8H$_2$O to yield 15.3 grams of a crystalline solid having the empirical formula Zr(O$_3$PCH$_2$COOH)$_2$ with an interlayer spacing of 11.1 Å.

EXAMPLE 17

The procedure of Example 1 was repeated except there was reacted 5.64 grams of morpholinomethylphosphonic acid in ethanol with 5.0 grams of ZrOCl$_2$.8H$_2$O to yield 6.1 grams of a crystalline solid having the empirical formula

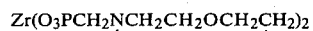

Zr(O$_3$PCH$_2$NCH$_2$CH$_2$OCH$_2$CH$_2$)$_2$ with an interlayer spacing of 16 Å.

EXAMPLE 18

Following the procedure of Example 1, there was reacted 7.4 grams of 2-sulfoethylphosphonic acid with 5.0 grams of ZrOCl$_2$.8H$_2$O to yield 6.1 grams of an amorphous solid having the empirical formula Zr(O$_3$PCH$_2$CH$_2$SO$_3$H)$_2$.

EXAMPLE 19

As in Examle 1, 13.3 grams of ethylene bisphosphonic acid was reacted with 5.6 grams of ZrOCl$_2$.8H$_2$O to yield 3.7 grams of crystalline inorganic polymeric solid having ethylene units bridging P atoms of the adjacent lamina with an interlayer spacing of 6.92 Å.

EXAMPLE 20

As in Example 1, 4.9 grams of phenoxymethylphosphonic acid was reacted with 3.7 grams of ZrOCl$_2$.8H$_2$O to yield 4.3 grams of a crystalline solid having the empirical formula Zr(O$_3$PCH$_2$OC$_6$H$_5$)$_2$ with an interlayer spacing of 18 Å.

EXAMPLE 21

As in Example 1, 2.0 grams of a phosphonic acid of the formula

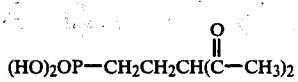

is reacted with 0.93 gram of $ZrOCl_2$ to yield 1.87 grams of a crystalline solid of the empirical formula

with an interlayer spacing of 11.3 Å.

EXAMPLE 22

As in Example 1, 9.45 grams of 2-bromoethyl phosphonic acid was reacted with 6.2 grams of $ZrOCl_2 \cdot 8H_2O$ to yield 8.5 grams of a solid having the empirical formula $Zr(O_3PCH_2CH_2Br)_2$ and a layer spacing of 13 Å.

EXAMPLE 23

As in Example 1, there was reacted 6.3 grams of $(HO)_2OP\text{-}OCH_2CH_2CN$ added as $BaO_3POCH_2CH_2CN \cdot 2H_2O$ in aqueous HCl with 1.1 grams of $ZrOCH_2 \cdot 8H_2O$ to yield 1.35 grams of a solid having the empirical formula $Zr(O_3POCH_2CH_2CN)_2$ with an interlayer spacing of 13.2 Å.

EXAMPLE 24

As in Example 1, there was reacted 4.6 grams of $(HO)_2OPCH_2CN$ added to water as the diethyl ester and hydrolyzed in situ to the acid with 4.3 grams of $ZrOCl_2 \cdot 8H_2O$ to form 4.6 grams of a crystalline precipitate having the empirical formula $Zr(O_3PCH_2CN)_2$.

EXAMPLE 25

As in Example 1, there was reacted 3.15 grams of $(HO)_2OPOC_6H_4NO_2$ added as the sodium salt in hydrochloric acid with 1.32 grams of $ZrOCl_2 \cdot 8H_2O$ to yield 1.66 grams of a crystalline precipitate having the empirical formula $Zr(O_3POC_6H_4NO_2)_2$ with an interlayer spacing of 15.8 Å.

EXAMPLE 26

Example 25 was repeated except the amount of the phosphoric acid ester was reduced to 3.03 grams and reacted with 2.21 grams of $Th(NO_3)_4 \cdot 4H_2O$ to yield 1.66 grams of a crystalline precipitate having the empirical formula $Th(O_3POC_6H_4NO_2)_2$ with an interlayer spacing of 16.4 Å.

EXAMPLE 27

Phosphorous acid, phenyl phosphonic acid and a zirconium salt were reacted in a molar ratio of 2:4:3 to yield a crystalline solid having the empirical formula $Zr[O_3P(H)_{1/3}(C_6H_5)_{2/3}]_2$ having an interlayer distance of 15.7 Å. The infrared spectra of this product is compared to the infrared spectra for $Zr(O_3PH)_2$ and $Zr(O_3PC_6H_5)_2$ in FIG. 9.

EXAMPLE 28

Diethyl 2-carboethoxyethyl phosphonate was prepared by the Arbuzov reaction of triethyl phosphite and ethyl 3-bromopropionate. The phosphonate ester product was hydrolyzed to the acid in refluxing HBr and then reacted in situ with zirconium ion. The resultant layered compound, zirconium 2-carboxyethyl phosphonate, has interlamellar carboxylic acid substituents. The highly crystalline modification had an interlayer distance of 12.8 Å and its n-hexylammonium salt was determined to have an interlayer distance of 27.2 Å. Thorium 2-carboxyethyl phosphonate was also prepared in an analogous manner.

The interlamellar carboxylic acid was determined to have a strong carbonyl stretching frequency at 1710 $cm^{-1}$. Upon sodium salt formation this shifts to 1575 and 1465 $cm^{-1}$. The x-ray powder pattern of the sodium salt indicates a layer spacing of 14.2 Å. The x-ray and infrared data of the interlamellar carboxylic acid and its salts indicate that this material behaves as a carboxylic acid. The ir behavior is analogous to that of ion exchange resins with carboxylic functionality.

The ion exchange behavior of the interlamellar carboxylic acid was investigated with a number of metals. FIG. 10 represents the pH vs. loading profile for the $2H^+\text{-}M^{+2}$ exchange of $Cu^{+2}$, $Ni^{+2}$, and $Co^{+2}$ with semicrystalline zirconium 2-carboxyethyl phosphonate. These profiles are in the normal pH range for the exchange of these metals with carboxylic acids.

The influence of crystallinity of the $H^+\text{-}Cu^{+2}$ exchange equilibrium is demonstrated in FIG. 11. The $pH_{0.5}$ is about 3.8 for the semi-crystalline and about 4.5 for the highly crystalline. This indicates that the matrix supporting the anchored functional group influences the reactivity of the functional group.

The interlamellar metal ion also has an influence on the $H^+/Cu^{+2}$ exchange equilibrium. High crystallinity modifications of thorium and zirconium 2-carboxyethylphosphonate were compared. This data is presented in FIG. 12. The thorium compound is the stronger acid by about 0.3 pKa units in this reaction ($pH_{0.5} = 4.2$ vs 4.5).

EXAMPLE 29

The reaction rate of zirconium 2-carboxyethylphosphonate with aqueous sodium hydroxide was determined by its addition to an aqueous solution of NaOH with decrease in pH measured as a function of time. As shown in FIG. 13, the concentration of hydroxide ion changed by over three orders of magnitude in 15 seconds representing reaction of 80% of the carboxylic groups. This established that the interlamellar reaction was quite facile and diffusion into the crystal did not involve a high kinetic barrier. Prolonged exposure at a pH of about 9 to 10 or higher, however, resulted in hydrolysis of the crystal with formation of $ZrO_2$.

EXAMPLE 30

Titanium phenylphosphonate having a surface area of about 151-167 $m^2/g$ was evaluated as a sorption solid. A sample of water was contaminated with 1-hexanol (1700 ppm), chloroform (1100 ppm) and benzene (300 ppm). One hundred ml of this solution was treated with 2.4 g of the titanium phenylphosphonate. Analysis established that the solid absorbed the organics. The distribution co-efficients were 750 (benzene), 430 (1-hexanol) and 250 ($CHCl_3$). Absorption of benzene was preferred.

EXAMPLE 31

Solid zirconium 2-bromoethyl phosphonate was slurried in an aqueous solution of 2-carboxyethyl phosphonic acid. A trace (1% mol) of HF was added and the mixture refluxed overnight. The infrared spectrum of the solid after this period definitely showed the presence of the carboxylic acid carbonyl band at 1710 cm$^{-1}$. The x-ray powder pattern of the exchanged product was virtually identical to the starting material. This was likely due to the fact that zirconium 2-bromoethyl phosphonate has an interlayer spacing of 13.0 Å and the 2-carboxy analog 12.8 Å. Based on stoichiometry, about 5 to 10% of the sites were exchanged. This being more than the apparent surface site, interlamellar exchange took place.

EXAMPLE 32

As in Example 1, 14 g of 3-sulfopropylphosphonic acid (prepared by the addition of diethylphosphite to propane sulfone followed by hydrolysis) was added 9 g of $ZrOCl_2.8H_2O$ yielding 10.1 g of a solid having the formula $Zr(O_3PCH_2CH_2CH_2SO_3H)_2$ and a d-spacing of 18.8 Å.

EXAMPLE 33

In the following table are listed other compounds which have been prepared by the method given in Example 1.

| Compound Produced | Phosphonic Acid Used | $M^{+4}$ Salt Used | Wt. Product |
|---|---|---|---|
| $ZR(O_3PCH_2CH_2CH_2PO_3)_1$ | 0.79 g $H_2O_3PCH_2CH_2CH_2PO_3H_2$ | 0.68 g $ZrOCl_2$ | 1.05 g |
| $ZR(O_3PCH_2CH_2CH_2PO_3H_2)_2$ | 0.79 g $H_2O_3PCH_2CH_2CH_2PO_3H_2$ | 0.34 g $ZrOCl_2$ | 0.45 g |
| $Ti_\frac{1}{2}Th_\frac{1}{2}(O_3P-C_6H_5)_2$ | 1.17 g $H_2O_3P-C_6H_5$ | 1.66 g 30% $TiOCl_2$ 2.05 g $Th(NO_3)_4$ | 2.35 g |
| $Th(O_3P-CH_3)_2$ | 0.845 g $H_2O_3P-CH_3$ | 2.25 g $Th(NO_3)_4$ | 1.7 g |
| $Zr(O_3P-CH_3)_2$ | 0.814 g $H_2O_3PCH_3$ | 0.75 g $ZrOCl_2$ | 0.87 g |
| $Th(O_3PCH_2OH)_2$ | 0.522 g $H_2O_3PCH_2OH$ | 1.35 $Th(NO_3)_4$ | 1.12 g |
| $Th(O_3P-C_{18}H_{37})_2$ | 0.95 g $(CH_3O)_2OPC_{18}H_{37}$ | 0.76 g $Th(NO_3)_4$ | 1.1 g |
| $Ti(O_3P-C_6H_4-OCH_3)_2$ | 0.98 g $H_2O_3P-C_6H_4OCH_3$ | 1.17 g 30% $TiOCl_2$ | 0.9 g |
| $U(O_3P-C_6H_5)_2$ | 1.29 g $H_2O_3P-C_6H_5$ | 1.55 g $UCl_4$ | 2.04 g |
| $Zr[O_3P(CH_2)_3CO_2H]_2$ | 51.9 g $H_2O_3P(CH_2)_3CO_2H$ | 49.7 g $ZrOCl_2$ | 56.7 g |
| $Zr[O_3P(CH_2)_4CO_2H]_2$ | 25.5 g $H_2O_3P(CH_2)_4CO_2H$ | 22.6 g $ZrOCl_2$ | 25.3 g |
| $Zr(O_3PCH=CH_2)_2$ | 12.0 g $Na_2O_3PCH=CH_2$ | 23.9 g $ZrOCl_2$ | 11.6 g |
| $Ti(O_3PCH=CH_2)_2$ | 9.44 g $Na_2O_3PCH=CH_2$ | 16.3 g $TiCl_4$ | 7.1 g |
| $Th(O_3PCH=CH_2)_2$ | 10.6 g $Na_2O_3PCH=CH_2$ | 21.0 g $Th(NO_3)_4$ | 7.9 g |

EXAMPLE 34

In the following table are listed the sources of the intermediate phosphonic acid or monoester phosphoric acids for the preceeding examples.

| Intermediate | Example No. | Source |
|---|---|---|
| $H_2O_3PCH_2CH_2CO_2H$ | 1, 2, 15 | Hydrolysis of Triethylester (McConnell et al, JACS, 78, 4453 (1956)) |
| $H_2O_3PCH_2Cl$ | 3, 4, 5, 6, 7 | Supplied by PCR, Inc. |
| $H_2O_3P-C_6H_5$ | 8, 9, 10, 11, 33 | Supplied by Aldrich Chemicals. |
| $H_2O_3PCH_2SH$ | 12 | $(C_2H_5O)_2OPCH_2Cl$ + Thiourea reaction followed by hydrolysis. |
| $H_2O_3PCH_2CH_2SH$ | 13 | $(C_2H_5O)_2OPCH=CH_2$ + $CH_3COSH$ followed by hydrolysis. |
| $H_2O_3PCH_2CH_2NH_2$ | 14 | Purchased from Calbiochem-Behring Corp. |
| $H_2O_3PCH_2CO_2H$ | 16 | Hydrolysis of Triethylester supplied by Aldrich. |
| $H_2O_3PCH_2NCH_2CH_2OCH_2CH_2$ (cyclic) | 17 | Field, JACS, 74, 1528 (1952). |
| $H_2O_3PCH_2CH_2SO_3H$ | 18 | Arbuzov reaction of $(C_2H_5O)_3P$ with $NaSO_3C_2H_4Br$ followed by hydrolysis. |
| $H_2O_3PCH_2CH_2PO_3H_2$ | 19 | Arbuzov reaction of $(C_2H_5O)_3P$ with $BrCH_2CH_2Br$ followed by hydrolysis. |
| $H_2O_3P-CH_2OC_6H_5$ | 20 | Walsh et al, JACS, 78, 4455 (1956) |
| $H_2O_3P(CH_2)_2CH_2(\overset{O}{\overset{\|}{C}}CH_3)_2$ | 21 | Reaction of Na acetylacetonate with $(C_2H_5O)_2OPCH_2CH_2Br$ followed by hydrolysis. |
| $H_2O_3PCH_2CH_2Br$ | 22 | Hydrolysis of diethylester supplied by Aldrich. |
| $H_2O_3POCH_2CH_2CN$ | 23 | Hydrolysis of $Ba^{+2}$ salt supplied by Aldrich. |
| $H_2O_3PCH_2CN$ | 24 | Hydrolysis of diethylester supplied by Aldrich. |
| $H_2O_3POC_6H_4NO_2$ | 25, 26 | Hydrolysis of sodium salt supplied by Aldrich. |
| $H_2O_3P(CH_2)_3SO_3H$ | 32 | Addition of $(C_2H_5O)_2PONa$ to propane sulfone followed by hydrolysis. |
| $H_2O_3P(CH_2)_nCO_2H$ n = 3, 4 | 33 | Arbuzov reaction of $(C_2H_5O)_3P$ and w-bromocarboxylate ester followed by hydrolysis. |
| $H_2O_3PCH=CH_2$ | 33 | Hydrolysis of ester supplied by Aldrich. |
| $H_2O_3P-C_6H_4OCH_3$ | 33 | Purchased from Alfa Inorg. |
| $H_2O_3PC_{18}H_{37}$ | 33 | Hydrolysis of dimethylester purchased from Alfa. |

-continued

| Intermediate | Example No. | Source |
|---|---|---|
| $H_2O_3PCH_2OH$ | 33 | Purchased from Alfa. |
| $H_2O_3PCH_3$ | 33 | Purchased from Alfa. |
| $H_2O_3P(CH_2)_3PO_3H$ | 33 | Purchased from Alfa. |

EXAMPLE 35

Using a Quantasorb surface area analyzer and pycnometer, the following measurements were made:

| Compound | Density | Surface Area |
|---|---|---|
| $Ti(O_3PC_6H_5)_2$ | 1.642 g/cc | 151.5 m²/g |
| $Zr(O_3PC_6H_5)_2$ | 1.828 g/cc | 185.9 m²/g |
| $Zr(O_3PCH_2CH_2PO_3)$ | 2.400 g/cc | 55.12 m²/g |
| $Zr(O_3PCH_2CH_2CO_2H)_2$ | 2.090 g/cc | 26.15 m²/g |
| $Th(O_3PC_6H_5)_2$ | 2.519 g/cc | 66.9 m²/g |
| $Th(O_3PCH_2Cl)_2$ | 3.284 g/cc | 9.73 m²/g |

These data demonstrate the high surface area of the products prepared, and also the densities verify a common structure.

EXAMPLE 36

Using the method outlined in Example 1, the following compounds are prepared:

1. $M[O_3P-(CH_2)_n-PR_2]_2$;    $M = Ti^{+4}, Zr^{+4}, Hf^{+4}, U^{+4}, Th^{+4}, Ce^{+4}, Pb^{+4}$; $n = 1-10$; $R = -CH_3, -C_2H_5, -C_6H_5$.

2. $M[O_3P-(CH_2)_n-OP(OR)_2]_2$;    M, n, R as above.

3. $M[O_3P-(CH_2)_n-\overset{+}{N}(CH_3)_3X^-]_2$;    M, n, as above; X = halide, sulfate nitrate, phosphate, acetate.

4. $M[O_3P-(CH_2)_n-NH-CS_2H]_2$;    M, n, as above.

5. $M[O_3P(CH_2)_n-N(CH_2CO_2H)_2]_2$;    M, n, as above.

6. $M[O_3P(CH_2)_n-\overset{+}{NH_2}-(CH_2)_3SO_3^-]_2$;    M, n, as above.

7. $M[O_3P-(CH_2)_n-NC]_2$;    M, n, as above.

8. $M[O_3P-(CH_2)_n-C\equiv CH]_2$;    M, n, as above.

9. $M[O_3P-O-\text{(phenyl)}]_2$;    M as above.

10. $M[O_3P-(CH_2)_n-\text{(bipyridyl)}]_2$;    M, n, as above.

11. $M[O_3P-(CH_2)_n-SR]_2$;    M, n, as above; $R = -CH_3, -C_2H_5$.

12. $M[O_3P-(CH_2)_n-\text{(cyclopentadienyl)}]_2$;    M, n, as above.

13. $M[O_3P-(CH_2)_n\overset{O}{\overset{\parallel}{C}}H]_2$;    M, n, as above.

14. $M[O_3P-(CH_2)_n-\text{(phenyl-Cl)}]_2$;    M, n, as above.

15. $M[O_3P-(CH_2)_n-\text{(ferrocenyl)}]_2$;    M, n, as above.

16. $M[O_3P-(CH_2)_n-C(SH)=CH(SH)]_2$;    M, n, as above.

17. $M[O_3P-(CH_2)_n-\text{(phenyl-R)}]$;    M, n, as above, $R = -CH_3, -C_2H_5, -CH(CH_3)_2$ or $-C(CH_3)_3$. as in 1.

18. $M[O_3P-(CH_2)_nOPR_2]_2$;    M, n and R as in 1.

19. $M[O_3P-(CH_2)_n-BR_2]_2$;    M, n, and R as in 1, or R = H.

20. $M[O_3P-(CF_2)_n-SO_3H]_2$;    M, n, as above.

21. Compounds above in which the $P-(CH_2)_n$ linkage is replaced by a $P-O-(CH_2)_n$ link.

Compounds 1, 2, 4, 7, 8, 9, 10, 11, 12, 16, and 18 are useful as complexers for immobilization of catalytically active metals, such as $Pd^{+2}$, $Ir^{+1}$, $Rh^{+1}$ $Ru^{+2}$, $Os^{+2}$.

Compounds 3, 4, 5, 6, 8, and 20 are useful as salt or ion exchangers.

Compound 13 is useful as an $H_2S$ scrubber.

Compounds 14 and 17 are useful sorbants.

Compound 15 is an electron transfer agent.

Compound 20, like the product in example 32, is useful as a solid acid catalyst.

The oxy acids of phosphorus which are used as intermediates in this example are obtained by known processes such as those indicated in Example 34.

EXAMPLE 37

Using the method outlined in Example 1, the following compounds are prepared:

1. $Zr(O_3PCH_2Cl)_2$
2. $Th(O_3PCH_2Cl)_2$
3. $Pb(O_3PCH_2Cl)_2$
4. $U(O_3PCH_2Cl)_2$
5. $Ti(O_3PCH_2Cl)_2$
6. $Zr(O_3PCH_2CH_2Cl)_2$
7. $Zr(O_3P-\text{phenyl})_2$
8. $Th(O_3P-\text{phenyl})_2$
9. $Ce(O_3P-\text{phenyl})_2$ -continued 10. 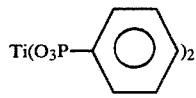

11. 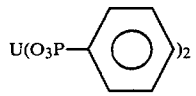

12. 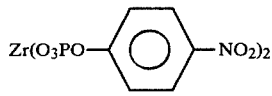

13. 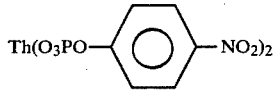

14. Zr(O₃POCH₂CH₂CN)₂
15. Zr(O₃PCH₂SH)₂
16. Zr(O₃PCH₂CH₂COOH)₂
17. Th(O₃PCH₂CH₂COOH)₂
18. Zr(O₃PCH₂COOH)₂

19. 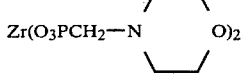

20. Zr(O₃PCH₂CH₂SO₃H)₂
21. Zr(O₃PCH₂CH₂CH₂SO₃H)₂
22. Ti(O₃PCH₂CH₂CH₂SO₃H)₂
23. Zr(O₃PCH₂)₂

24. 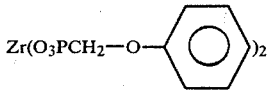

25. Zr(O₃PCH₂CH₂SH)₂
26. Zr(O₂PCH₂CH₂Br)₂
27. Zr(O₃PCH₂CH₂NH₂)₂
28. Zr(O₃PCH₂CN)₂
29. Zr(O₃PCH₂CH₂CH₂COOH)₂
30. Zr(O₃PCH₂CH₂CH₂CH₂COOH)₂
31. ZrO₃PCH₂CH₂CH₂PO₃
32. Ti(O₃PCH₃)₂
33. Th(O₃PCH₃)₂
34. Zr(O₃PCH₃)₂
35. Th[O₃P(CH₂)₁₇CH₃]₂

36. 

37. 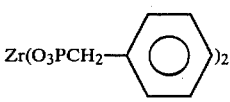

38. Zr(O₃PCH₂SCH₂CH₃)₂

39. 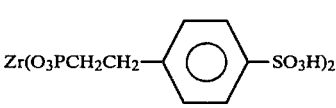

40. Zr(O₃PCH₂CHCH₂)₂
41. ZrO₃P(C₁₀H₂₀)PO₃
42. Th(O₃PCH₂OH)₂

-continued

43. 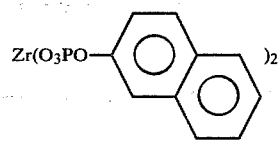

44. 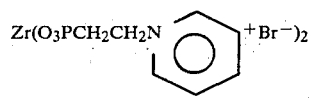

45. 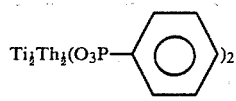

46. Zr(O₃POH)₃(O₃PCH₂CHCH₂)₄/₃
47. Zr[O₃P(C₁₀H₂₀)PO₃]₃(O₃POH)₄/₃

Compounds 7 and 10 are useful for absorbing organic compounds from aqueous media.

Compounds 14, 15, 25 and 28 are useful for absorbing $Cu^{+2}$ and $Ag^+$ from aqueous solution.

Compounds 16, 18, 29 and 30 are useful for loading $Cu^{+2}$, $Ni^{+2}$, and $Co^{+2}$.

Compounds 20 and 21 are useful for loading $Cu^{+2}$.

Other metal$^{+4}$ ions which are analogous to $Zr^{+4}$ in the process to make phosphate and phosphonate analogs, are metals with approximately the same ionic radius as $Zr^{+4}$ (0.8 Å), for example,

| $Zr^{+4}$ | 0.08Å | $Te^{+4}$ 0.81 | $Pr^{+4}$ 0.94 | $Mn^{+4}$ 0.5 |
|---|---|---|---|---|
| $W^{+4}$ | 0.66 | $Sn^{+4}$ 0.71 | $Pb^{+4}$ 0.92 | $Ir^{+4}$ 0.66 |
| $U^{+4}$ | 0.89 | $Si^{+4}$ 0.41 | $Os^{+4}$ 0.67 | $Hf^{+4}$ 0.81 |
| $Ti^{+4}$ | 0.68 | $Ru^{+4}$ 0.65 | $Nb^{+4}$ 0.67 | $Ge^{+4}$ 0.53 |
| $Th^{+4}$ | 0.95 | $Pu^{+4}$ 0.86 | $Mo^{+4}$ 0.68 | $Ce^{+4}$ 1.01 |

The thio analogs of the phosphonates and phosphates can also be made by this process. The larger, more readily redoxable elements can lead to semiconducting, photoactive supports. All of the above noted solid, layered compounds can be useful as a chromatographic solid phase, adsorbants ion-exchange and hosts or carriers for controlled release of active substances.

In the preparation of anchorable Layered Compounds, a general approach to zirconium phosphate and the other zirconium compositions described herein and in the applications incorporated herein involve the following concepts:

(1) Tetrahedral anions with 3-metal coordinating groups and one interlayer group desirable

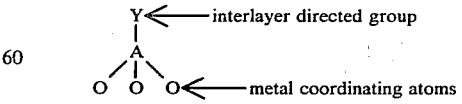

(2) Charge on anion should be $-1$, $-2$, $-3$ (charge on metal ion therefore should be $+2$, $+4$, $+6$ for M[O₃AY]₂ stoichiometry needed for sandwiching and bridging configuration)

(i) for $-1$ charge, conjugate acid of anion is

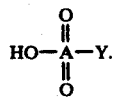

"A" can be S (or Se, Cr, Mo, W, etc., (+6 forming elements)

(ii) for −2 charge, conjugate acid of anion

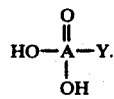

"A" can be P, As, Sb, V, Nb, Ta, etc., (+5 forming elements)

(iii) for −3 charge, conjugate acid of anion is

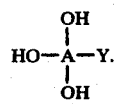

"A" can be Si, Ge, Ti, Zr, Sn, Pb (+4 forming elements).

Some exemplary salts which meet these criteria are listed below.

$M[O_3A-Y]_2$: Examples of compounds of structure which can form layered host structures analogous to zirconium phosphate and the phosphorus or arsenic containing compounds of the applications incorporated herein:

(1) $[O_3A-Y]^{-1}$  A = S, for example, Y = $NH_2$ (conjugate acid is sulfamic acid)

M+ = $Cu^{+2}$, $Zn^{+2}$, $Fe^{+2}$, alkaline earths

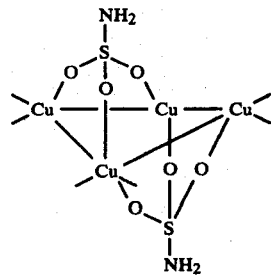

(2) $[O_3A-Y]^{-2}$  Zirconium phosphate prototypes (A = P, As, Sb, etc.)

(3) $[O_3A-Y]^{-3}$  A = Si, for example, Y = $OCH_2CN$

M = $Mo^{+6}$

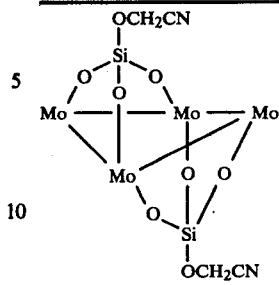

In all cases, metal ion is in octahedral sphere (could be trigonal prism)

Although the structure of these solid phases is polymeric in nature, it is convention in solid inorganic nomenclature to refer to them by their monomeric units.

What is claimed is:

1. A process for the production of phosphorus-containing organo substituted inorganic polymers which comprises reacting in a liquid medium at least one organophosphorous or organophosphoric acid compound of the formula:

$[(HO)_2OP]_nR$ or $[(HO)_2OPO]_nR$ wherein n is 1 or 2 and R is an organo group covalently coupled to phosphorus and wherein when n is 2, R contains at least two carbon atoms and is directly or indirectly coupled to the phosphorus atoms through different carbon atoms whereby the two phosphorus atoms are separated by at least two carbon atoms, with at least one tetravalent metal ion to precipitate, from the liquid medium, a solid inorganic polymer in which the molar ratio of phosphorus to tetravalent metal is about 2 to 1 and in which the organo group is covalently bonded to phosphorus and phosphorus is linked to the tetravalent metal through oxygen.

2. Organo substituted inorganic polymers as prepared by the process of claim 1.

3. Solid inorganic phosphorus-containing polymers providing pendant organo groups, and which contain structural units of the formula:

$M(O_3PR)_2$ or $M(O_3POR)_2$ wherein R is a halogen containing organo group, the three oxygens bonded to phosphorus are structurally linked to one or more tetravalent metal, M, selected from the group consisting of titanium, zirconium, cerium, hafnium, lead, thorium and uranium, and wherein the molar ratio of phosphorus to tetravalent metal is about 2 to 1.

4. Solid inorganic phosphorus-containing polymers providing pendant organo groups, and which contain structural units of the formula:

$M(O_3PR)_2$ or $M(O_3POR)_2$ wherein R is an amino-containing organo group, the three oxygens bonded to phosphorus are structurally linked to one or more tetravalent metal, M, selected from the group consisting of titanium, zirconium, cerium, hafnium, lead, thorium and uranium, and wherein the molar ratio of phosphorus to tetravalent metal is about 2 to 1.

* * * * *